United States Patent [19]

Bruynes et al.

[11] 4,366,315
[45] Dec. 28, 1982

[54] PROCESS FOR PREPARING 3'BROMO-DESACETOXYCEPHALOSPORANIC ACID SULFOXIDE COMPOUNDS

[75] Inventors: Cornelis A. Bruynes, Koudekerk; Theodorus K. Jurriens, Delft, both of Netherlands

[73] Assignee: Gist-Brocades N.V., Delft, Netherlands

[21] Appl. No.: 234,545

[22] Filed: Feb. 13, 1981

[30] Foreign Application Priority Data

Feb. 14, 1980 [GB] United Kingdom ............... 8004925

[51] Int. Cl.³ .................. C07D 501/04; A61K 31/545
[52] U.S. Cl. ......................... 544/16; 544/30; 544/24; 424/246; 544/22; 544/26
[58] Field of Search .................. 544/16, 22, 28, 30; 424/246

[56] References Cited

U.S. PATENT DOCUMENTS 3,922,268 11/1978 Murphy et al. ............ 544/16
4,182,870 1/1970 Bruynes et al. ............ 544/16
4,223,135 9/1980 Walker et al. ............ 544/16

FOREIGN PATENT DOCUMENTS

72/12992 4/1973 Netherlands .
1326531 8/1973 United Kingdom .

Primary Examiner—Nicholas S. Rizzo
Attorney, Agent, or Firm—Hammond & Littell, Weissenberger and Muserlian

[57] ABSTRACT

An improved process for the preparation of 3'-bromo-desacetoxycephalosphoranic acid sulfoxide compounds comprising protecting the 4-carboxy group of a 3'-unsubstituted cephalosporanic acid sulfoxide by silylating in an inert anhydrous organic solvent and brominating the silylated compound in situ which 3'-bromo compounds are valuable intermediates for the preparation of therapeutically useful cephalosporanic acid compounds.

16 Claims, No Drawings

PROCESS FOR PREPARING 3'BROMO-DESACETOXYCEPHALOSPORANIC ACID SULFOXIDE COMPOUNDS

STATE OF THE ART

Processes comprising protection of the carboxy group and subsequent bromination of 3'-unsubstituted desacetoxycephalosporanic acid sulfoxide compounds are known from the literature; see, for instance, British Patent Specification No. 1,326,531. Usually, the carboxy group is protected by esterification with alcohols derived from aliphatic or aromatic hydrocarbons and, firstly, this implies that the carboxy group must be esterified before the bromination is carried out and, secondly, that at a later stage in the process of preparing therapeutically useful compounds, the ester group must be reconverted into the carboxy group. Thus, two separate reactions must be carried out in case hydrocarbon ester protection is applied, which makes the process laborious and lowers the overall yield.

OBJECTS OF THE INVENTION

It is an object of the invention to provide an improved process for the preparation of 3'-bromo-desacetoxycephalosporanic acid compounds in good yields without isolation of the intermediate product.

This and other objects and advantages of the invention will become obvious from the following detailed description.

THE INVENTION

The novel process of this invention for the preparation of 3'-bromo-desacetoxycephalosporanic acid sulfoxide compounds comprises protecting the 4-carboxy group in 3'-unsubstituted cephalosporanic acid sulfoxide by silylating in an inert anhydrous organic solvent and brominating the silylated compound in situ.

Thus, the invention provides a process wherein it is not necessary to isolate an intermediate product before the bromination is carried out and the introduction and the removal of the protective silyl group can be carried out quickly and smoothly and, moreover, proceeds virtually without loss of product. The British patent specification mentioned above contains only one example of a process in which silyl protection of the carboxy group has been used, but that particular example demonstrates that apparently a time-consuming procedure of isolation and thorough drying of the silyl-protected intermediate is necessary before the bromination can be carried out. Dutch patent application Ser. No. 72,12992 discloses a process in which the intermediate silyl compound is not isolated before the bromination is effected. When this method is used, however, the bromine compound is obtained in a poor yield only.

The process of the present invention compares favorably with the prior art processes in that no intermediates have to be isolated which implies that the process proceeds smoothly and efficiently as a so-called "one-pot procedure" and the 3'-bromo-desacetoxy-cephalosporanic acid sulfoxide derivatives are obtained in excellent yields.

The process of the invention is effected in an inert solvent and it is to be understood that the term "inert solvent" as used in this specification implies that the solvent does not interfere with the silylation or with the bromination reaction. Examples of suitable solvents are alkyl and aryl halides, such as 1,2-dichloroethane, dichloromethane, chloroform, chlorobenzene and o-dichlorobenzene; benzene; nitrobenzene; esters like ethyl acetate, methyl acetate and ethyl formate and siloxanes like hexamethyldisiloxane and/or mixtures thereof. The desacetoxycephalosporanic acid sulfoxide derivatives are practically insoluble in these organic solvents so that they form a suspension. It is necessary, however, that the starting material is at least to some extent soluble in the solvent used and on completion of the silylation, a clear solution is usually obtained.

Suitable reaction temperatures range from −40° to 80° C., but preferably the reaction is carried out at a temperature between −10° and 20° C. The time required for the silylation reaction varies from a few minutes to several hours depending on the reaction conditions, the silylating agent and the starting material used. The reaction is preferably carried out under a dry, inert gas, such as nitrogen atmosphere.

The silylation is preferably effected with a silylating agent comprising a silyl group of the formula:

in which R', R" and R''' are the same or different and each represents an alkyl group with at most 6 carbon atoms, which may be substituted with a halogen atom, or an aryl group with the trimethylsilyl group being particularly preferred.

Examples of suitable silylating agents are silazanes and silyl compounds derived from urea, amides, imides, phosphorimidates, sulfonamides, sulfuric acid, amidosulfonates, carbamates, hydantoins and 2-oxazolidinones and/or mixtures thereof. The following agents may, for instance, be used alone and/or in mixtures:

hexamethyldisilazane
N,N'-bis-(trimethylsilyl)-urea
N,O-bis-(trimethylsilyl)-acetamide
diethyl trimethylsilyl trimethylsilylphosphorimidate
trimethylsilyl trimethylsilylamidosulfonate
N-methyl-N-trimethylsilyltrifluoroacetamide
N,O-bis-(trimethylsilyl)-trifluoroacetamide
N-methyl-N-trimethylsilylacetamide
bis-(trimethylsilyl)-sulfate
N,N-bis-(trimethylsilyl)-formamide
trimethylsilyl trimethylsilylcarbamate
N-trimethylsilylacetamide
N-trimethylsilylcaprolactam
bis-(trimethylsilyl)-bis-(trimethylsilyl)-ethanediimidate
N-trimethylsilylurethane
N-trimethylsilylphthalimide
N-trimethylsilylsuccinimide
N-trimethylsilyldiacetamide
N-trimethylsilylhexahydrophthalimide
1,3-bis-(trimethylsilyl)-5,5-dimethylhydantoin
trimethylsilyl-bis-(trimethylsilyl)-amidosulfonate
N-trimethylsilyltrichloroacetamide
N-trimethylsilylbenzamide
N-trimethylsilyl-2-oxazolidinone
1,3-bis-(trimethylsilyl)-hydantoin
N-trimethylsilyl-4-nitrobenzamide
N-trimethylsilyl-2,2-dimethylpropanamide, and
N-trimethylsilylbenzenesulfonamide.

Silylating agents containing a silicon-halogen bond such as chlorotrimethylsilane are less attractive since with these silylating agents, the addition of one equivalent of an amine such as triethylamine is necessary to bind the hydrogen halide generated in the reaction. The amount of amine is very critical and even a small excess of amine causes the bromination to take place at the 2-position (cf. Japanese patent application Ser. No. 49-33694).

The bromination may be carried out in a manner known per se for the introduction of a bromine atom at the 3'-position of a desacetoxy-cephalosporanic acid sulfoxide derivative. Examples of suitable brominating agents and N-bromoamides, N-bromoimides, N-bromohydantoins and N-bromo-2-oxazolidinones such as N-bromosuccinimide, N-bromophthalimide, 1,3-dibromo-5,5-dimethylhydantoin, 3-bromo-4,4-dimethyl-2-oxazolidinone, N-bromocaprolactam, N-bromoacetamide and N-bromo-3,3-dimethylglutarimide. Particularly preferred are N-bromosuccinimide and 1,3-dibromo-5,5-dimethylhydantoin which are easily obtainable. The bromination is preferably initiated by irradiating the reaction mixture, for instance with a tungsten lamp or another source of visible or ultraviolet light.

After the silylation has been effected, it is preferred to add an acid in an amount at least sufficient to neutralize any base or bases present in the reaction mixture. A large excess of acid should be avoided, however, as this may cause decomposition of the silyl-protected compound.

Suitable acids include carboxylic acids, sulfonic acids and inorganic acids. Preferably, the acid used is a lower carboxylic acid, a nitro- or halogen-substituted carboxylic acid, a sulfonic acid or a hydrogen halide. Examples of suitable acids are amidosulfonic acid, methanesulfonic acid, 10-camphorsulfonic acid, 4-chlorobenzenesulfonic acid, trichloroacetic acid, trifluoroacetic acid, formic acid, bromoacetic acid, 2-chlorobenzoic acid, 4-nitrobenzoic acid, 4-nitrophenylacetic acid, α-chlorophenylacetic acid, p-toluenesulfonic acid, sulfuric acid, hydrogen chloride and hydrogen bromide. Amidosulfonic acid is particularly preferred.

Particularly useful compounds that may be produced by the process of the invention are 7-acylamino derivatives of the formula:

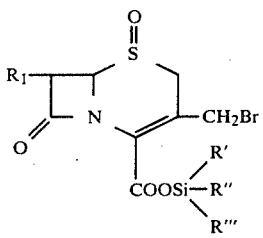

wherein $R_1$ represents an acylamino group and R', R" and R'" are as hereinbefore defined.

The acylamino group may be chosen from the groups hitherto disclosed in the chemical literature including patent specifications or known to those skilled in the art of penicillin or cephalosporin chemistry attached to the 6-position in natural or semisynthetic penicillin compounds or attached to the 7-position of natural or semisynthetic cephalosporin compounds. For instance, the acylamino group may be one of those forming the 6β- side chain of known penicillins such as phenylacetamido, phenoxyacetamido, benzamido and formamido. The choice of the acylamino group will depend on various factors such as availability of starting material, desired therapeutically active compound and possible formation of undesired by-products.

The cephem sulfoxide starting materials can readily be obtained from the corresponding penicillins by known methods. For instance, a 6-acylaminopenicillanic acid anhydride sulfoxide may be heated with an anhydrous acid in the presence of an organo-silicon compound as described in British Pat. No. 1,409,415 to obtain the corresponding 7-acylamino-desacetoxy-cephalosporanic acid which is subsequently converted into its sulfoxide. Thus, starting materials for the process of the invention may easily be obtained from relatively inexpensive products like penicillin G.

The cephalosporanic acid starting material may contain reactive groups which can be attacked by reactants used in the reaction described. It will be understood that those groups must be protected. Suitable protective groups are known to those skilled in the art of penicillin or cephalosporin chemistry.

Common by-products of the bromination are compounds substituted by a bromine atom at the 2-position instead of or in addition to such an atom at the 3'-position. The 2,3'dibromo derivatives can easily be converted into the desired 3'-bromo derivative by the method described in European patent application Ser. No. 78200174.7 published under No. 0001149.

Similarly, the 2-bromo derivatives can be converted by the same process into the corresponding 2-unsubstituted compound which can be used again as the starting material in the process of the invention, thus preventing loss of starting material in the form of undesired by-products.

According to this method, debromination at the 2-position is effected by treating the reaction mixture with a debrominating agent capable of replacing in the presence of a hydrogen donor the bromine atom at the 2-position by hydrogen.

The 3'-bromo derivatives prepared by the process of the invention may be converted into therapeutically or otherwise useful cephalosporines by (a) replacing the bromine atom with a desired substituent; (b) reducing the sulfoxide group; (c) removing the silyl group; (d) if desired replacing the acyl group of the 7-acylamino substituent by another acyl group. Methods to carry out said reactions are described in the literature. The following are mentioned by way of example.

ad a. The bromine atom may be replaced by a different substituent by a nucleophilic substitution reaction, for instance by reacting the brominated compound with an alkali metal thiolate and the reaction may be carried out conveniently in the reaction mixture obtained after the bromination step. Thus, it is another advantage of the process of the invention that it is not necessary to isolate and purify the brominated compound before replacing the bromine atom by a different substituent at the 3'-position.

ad b. The sulfoxide may be reduced with phosphorus trichloride or tribromide.

ad c. The silyl group can easily be removed by reacting the compound with compounds containing active hydrogen such as water and alcohols and the removal of the silyl group may also take place concurrently with one of the other reactions.

ad d. Suitable methods for the deacylation of 7-acylaminocephalosporins are described in the literature, e.g. British Pat. No. 1,041,985 and No. 1,119,806, Belgian Patent No. 719,712, and South African patent No. 68/5048 and No. 68/5327. Acylation of the 7-amino derivatives obtained may be carried out by using acylating agents described in the literature on penicillin and cephalosporin chemistry.

Examples of useful therapeutics that may be prepared from the products of the process of the invention are the well known antibiotics cefazolin, cefaloridine and cefamandole.

The yields of the 3'-bromo-cephalosporanic acid sulfoxide derivatives in the reaction mixtures were determined as follows. A weighed sample, withdrawn from the weighed reaction mixture, was added to an excess of an ethereal diazomethane solution containing about 10% of methanol. When nitrogen evolution stopped, the excess of diazomethane was destroyed by adding a small excess of glacial acetic acid. The solvents were evaporated in vacuo and the residue was dissolved in acetone and the volume of this solution was adjusted to a predetermined volume in a volumetric flask. A more detailed description is given in Example 1.

The concentration of the methyl ester of the 3'-bromo-cephalosporanic acid sulfoxide derivative in the solution thus obtained was determined by comparing it by means of High Performance Liquid Chromatography (HPLC) analysis with a reference solution containing a known concentration of the same compound. The concentration of this reference solution was determined by dissolving a weighed quantity of the methyl ester, prepared as described in the following "Preparation of Reference Compounds for HPLC Analysis" and analyzed by means of quantitative 300 MHz NMR analysis in a predetermined volume of acetone in a volumetric flask. The yields determined by this method of analysis have an accuracy of approximately 10%.

THE PREPARATION OF REFERENCE COMPOUNDS FOR HPLC ANALYSIS (a) Methyl 7-benzamido-3-methyl-3-cephem-4-carboxylate-1-oxide.

An excess of an ethereal diazomethane solution was added to an ice-cooled suspension of 5 gm of 7-benzamido-3-methyl-3-cephem-4-carboxylic acid-1-oxide in 150 ml of dichloromethane and the mixture was stirred for half an hour. Then, excess diazomethane was destroyed with acetic acid and methanol was added. The mixture was evaporated to dryness in vacuo and the residue was crystallized from methanol to obtain 4.5 gm (86.6% yield) of methyl 7-benzamido-3-methyl-3-cephem-4-carboxylate-1-oxide.

NMR Spectrum ($CF_3COOD$): 2.31 (s, 3H); 3.78, 3.84, 4.08, 4.14 (ABq, 2H, J 19.5 Hz); 4.10 (s, 3H); 5.23 (d, 1H, J 4.5 Hz); 6.43 (d, 1H, J 4.5 Hz); 7.54–7.93 (m, 5H, J 8 Hz).

IR Spectrum: 3315, 1790, 1732, 1643, 1530, 1249, 1238, 1039 $cm^{-1}$.

(b) Methyl 3-methyl-7-phenoxyacetamido-3-cephem-4-carboxylate-1-oxide was prepared by the same procedure starting from 3-methyl-7-phenoxyacetamido-3-cephem-4-carboxylic acid-1-oxide in 87.7% yield.

NMR Spectrum ($CDCl_3$-DMSO-D6): 2.08 (s, 3H), 3.64, 3.70, 3.71, 3.78 (ABq, 2H, J 16 Hz); 3.82 (s, 3H); 4.58, 4.63, 4.64, 4.69 (ABq, 2H, J 13.5 Hz); 4.95 (d, 1H, J 4.5 Hz); 5.99 (dd, 1H, J 4.5 and 9.5 Hz); 6.94, 6.97, 7.00, 7.02, 7.28, 7.31, 7.33 (m, 5H).

IR Spectrum: 3368, 1765, 1737, 1698, 1528, 1243, 1230, 1062, 1020 $cm^{-1}$.

(c) Methyl 7-formamido-3-methyl-3-cephem-4-carboxylate-1-oxide was prepared by the same procedure in 84.0% yield starting from 7-formamido-3-methyl-3-cephem-4-carboxylic acid-1-oxide.

NMR Spectrum ($CF_3COOD$): 2.32 (s,3H); 3.78, 3.85, 4.07, 4.13 (ABq, 2H, J 19.5 Hz); 4.10 (s, 3H); 5.15 (d, 1H, J 3.5 Hz); 6.36 (d, 1H, J 3.5 Hz); 8.50 (s, 1H).

IR Spectrum: 3320, 1780, 1730, 1725, 1645, 1540, 1230, 1023 $cm^{-1}$.

(d) Methyl 7-benzamido-3-bromomethyl-3-cephem-4-carboxylate-1-oxide.

1.2 g (6.8 mmoles) of N-bromosuccinimide were added to an ice-cooled solution of 1.4 g (4 mmoles) of methyl 7-benzamido-3-methyl-3-cephem-4-carboxylate-1-oxide in a mixture of 25 ml of dichloromethane and 50 ml of acetic acid. The mixture was stirred and irradiated with a 150 W tungsten lamp for 1.5 hours. The reaction mixture was poured into water and dichloromethane and the organic layer was separated and washed three times with 500 ml of water. After treatment with activated charcoal, it was dried over magnesium sulfate and filtered. The filtrate was concentrated to about 20 ml in vacuo and the product was precipitated by addition of 150 ml of diethyl ether. The mixture was filtered and the product was washed with diethyl ether. It was crystallized by dissolving it in 100 ml of refluxing dichloromethane and precipitation by addition of 100 ml of diethyl ether to obtain 1.0 g pure methyl 7-benzamido-3-bromomethyl-3-cephem-4-carboxylate-1-oxide (yield 58.8%).

NMR Spectrum ($CF_3COOD$): 3.94, 4.00, 4.31, 4.37 (ABq, 2H, J 19 Hz); 4.14 (s, 3H); 4.44, 4.48, 4.55, 4.58 (ABq, 2H, J 11 Hz); 5.27 (d, 1H, J 4 Hz): 6.48 (d, 1H, J 4 Hz); about 7.40 (m, 5H).

IR Spectrum: 3270, 1790, 1723, 1713, 1645, 1520, 1027 $cm^{-1}$.

(e) Methyl 3-bromomethyl-7-phenoxyacetamido-3-cephem-4-carboxylate-1-oxide was prepared in the same way in 33% yield by brominating methyl 3-methyl-7-phenoxyacetamido-3-cephem-4-carboxylate-1-oxide. The compound was purified by chromatography over silica gel using 10% acetone in dichloromethane as the eluent.

NMR Spectrum (DMSO-D6): 3.82, 3.89, 4.01, 4.08 (ABq, 2H, J<1 and 18.5 Hz); 3.88 (s, 3H); 4.51, 4.54, 4.60, 4.64 (ABq, 2H, J 10 Hz); 5.09 (dd, 1H, J<1 and 5 Hz); 6.13 (dd, 1H, J 5 and 9.5 Hz); 6.97–7.05, 7.32–7.37 (m, 5H); 8.24 (d, 1H, J 9.5 Hz).

IR Spectrum; 3390, 1790, 1736, 1730, 1700, 1530, 1250, 1233, 1024 $cm^{-1}$.

(f) Methyl 3-bromomethyl-7-formamido-3-cephem-4-carboxylate-1-oxide was prepared in 21% yield by brominating methyl 7-formamido-3-methyl-3-cephem-4-carboxylate-1-oxide by the method described for methyl 7-benzamido-3-bromomethyl-3-cephem-4-carboxylate-1-oxide under d.

NMR Spectrum (DMSO-D6): 3.81, 3.86, 3.99, 4.06 (ABq, 2H, J 19 Hz); 3.89 (s, 3H); 4.51, 4.55, 4.65, 4.68 (ABq, 2H J 10 Hz); 5.06 (d, 1H, J 5 Hz); 6.06 (dd, 1H,' J 5 and 9.5 Hz); 8.23 (s, 1H); 8.50 (d, 1H, J 9.5 Hz).

IR Spectrum: 3280, 1780, 1725, 1645, 1530, 1038 $cm^{-1}$.

In the following examples there are described several preferred embodiments to illustrate the invention. However, it is to be understood that the invention is not intended to be limited to the specific embodiments. Silylation was effected under a nitrogen atmosphere and bromination was carried out under irradiation with a 150 W tungsten lamp unless otherwise stated.

EXAMPLE 1

To a suspension of 356 mg (1.02 mmoles) of 3-methyl-7-phenylacetamido-3-cephem-4-carboxylic acid-1-oxide in 10 ml of 1,2-dichloroethane, which was kept under nitrogen and stirred magnetically, 0.15 ml of hexamethyldisilazane (0.72 mmole) was added and, after stirring for three hours at a temperature of 40°–45° C., a clear, slightly yellow solution was obtained. 30 ml of 1,2-dichloroethane were added to this solution cooled in an ice bath followed by 61 mg (0.63 mmole) of amidosulfonic acid. After stirring for 15 minutes, 249 mg of N-bromosuccinimide (1.40 mmoles) were added and the mixture was irradiated with a 150 W tungsten lamp for half an hour. The mixture was turbid then.

A sample of 3.20 g was taken from the reaction mixture of 48.90 g and was esterified by adding it to an excess of diazomethane in diethyl ether containing about 10% of methanol. When nitrogen no longer evolved, the excess of diazomethane was destroyed by the addition of acetic acid and the solvent was evaporated in vacuo. The residue was dissolved in acetone and the volume of the solution was adjusted to 50 ml. The concentration of methyl 3-bromomethyl-7-phenylacetamido-3-cephem-4-carboxylate-1-oxide in this solution was determined by means of HPLC analysis as hereinbefore described and found to be 0.31 mg/ml. From this data, a yield of 53% of trimethylsilyl 3-bromomethyl-7-phenylacetamido-3-cephem-4-carboxylate-1-oxide was calculated.

EXAMPLES 2–6

The procedure used was that described in Example 1, i.e. silylation of 3-methyl-7-phenylacetamido-3-cephem-4-carboxylic acid-1-oxide (I) was carried out in 10 ml of 1,2 dichloroethane with 0.72 mmole of hexamethyldisilazane, the solution was diluted with 1,2-dichloroethane to approximately 40 ml, amidosulfonic acid was added and bromination was carried out at ice-bath temperature using the brominating agents listed in Table 1 from which also further details can be obtained.

bromomethyl-7-phenylacetamido-3-cephem-4-carboxylate-1-oxide was 48%.

EXAMPLE 8

0.15 ml of hexamethyldisilazane (0.72 mmole) was added to a suspension of 350 mg (1.00 mmole) of 3-methyl-7-phenylacetamido-3-cephem-4-carboxylic acid-1-oxide in 10 ml of 1,2-dichloroethane. The obtained clear solution after stirring at 40°–45° C. for 2 hours was cooled in an ice-bath and diluted with 30 ml of 1,2-dichloroethane. After the addition of 82 ml (0.50 mmole) of trichloroacetic acid, bromination was carried out in one hour using 292 mg (1.64 mmoles) of N-bromosuccinimide as the brominating agent. The yield of trimethylsilyl 3-bromomethyl-7-phenylacetamido-3-cephem-4-carboxylate-1-oxide was 45%.

EXAMPLE 9

368 mg (1.06 mmoles) of 3-methyl-7-phenylacetamido-3-cephem-4-carboxylic acid-1-oxide were silylated with 122 mg (0.76 mmoles) of hexamethyldisilazane in 25 ml of dichloromethane by refluxing for 2 hours. To the clear, slightly yellow solution obtained, 0.09 mmole of hydrobromic acid (7 ml of a 0.013 molar solution in benzene) was added, the solution was diluted with dichloromethane to 40 ml and cooled in an ice bath. Bromination was carried out in half an hour using 283 mg (1.60 mmoles) of N-bromosuccinimide as the brominating agent. The yield of trimethylsilyl 3-bromomethyl-7-phenyl-acetamido-3-cephem-4-carboxylate-1-oxide was 47%.

EXAMPLE 10

349 mg (1.00 mmole) of 3-methyl-7-phenylacetamido-3-cephem-4-carboxylic acid-1-oxide were suspended in 10 ml of 1,2-dichloroethane and silylated by adding 0.23 ml (1.05 mmoles) of hexamethyldisilazane and stirring at 30°–35° C. for 1½ hours. After cooling in an ice-bath, 0.02 ml (0.3 mmoles) of methanesulfonic acid were added followed by 167 mg (0.94 mmole) of N-bromosuccinimide. After irradiation for 15 minutes, a second portion of 152 mg of N-bromosuccinimide (0.85 mmole) was added and irradiation was continued for 1½ hours. The yield of trimethylsilyl 3-bromomethyl-7-phenylacetamido-3-cephem-4-carboxylate-1-oxide was 52%.

TABLE I

| | | silylation | | | | time of | |
|---|---|---|---|---|---|---|---|
| Example | mmoles of I | temperature (°C.) | time (h) | mmole of $H_2NSO_3H$ | brominating agent (mmoles) | irradiation time (h) | yield % |
| 2 | 1.02 | 30–35 | 5 | 0.57 | N—bromophthalimide (1.68) | ½ | 45 |
| 3 | 1.00 | 30–35 | 5 | 0.56 | 1,3-dibromo-5,5-dimethyl-hydantoin (0.81) | ½ | 45 |
| 4 | 1.00 | 40–45 | 4 | 0.63 | 3-bromo-4,4-dimethyl-oxazolidinone-2 (1.53) | ½ | 53 |
| 5 | 1.02 | 40–45 | 3 | 0.57 | N—bromocaprolactam (1.56) | ½ | 52 |
| 6 | 1.00 | 40–45 | 2 | 0.57 | N—bromoacetamide (1.50) | ½ | 52 |

EXAMPLE 7

A mixture consisting of 370 mg (1.06 mmoles) of 3-methyl-7-phenylacetamido-3-cephem-4-carboxylic acid-1-oxide, 10 ml of dichloromethane and 0.14 ml (0.67 mmole) of hexamethyldisilazane was stirred and refluxed under nitrogen for 2.5 hours. 50 mg of amidosulfonic acid (0.52 mmole) were added to the slightly turbid solution obtained and bromination was carried out at ice-bath temperature in half an hour using 330 mg of N-bromo-3,3-dimethylglutarimide (1.50 mmoles) as the brominating agent. The yield of trimethylsilyl 3-

EXAMPLE 11

A mixture of 350 mg (1 mmole) of 3-methyl-7-phenylacetamide-3-cephem-4-carboxylic acid-1-oxide in 10 ml of 1,2-dichloroethane was silylated with 308 mg (1.51 mmoles) of N,N'-bis-(trimethylsilyl)-urea by stirring at 30° C. for 2 hours under nitrogen. The mixture was diluted to 40 ml with 1,2 dichloroethane and cooled in an ice-bath. 0.12 ml of trifluoroacetic acid (1.56 mmoles) was added and bromination was carried out in 1¼ hours using 290 mg (1.63 mmoles) of N-bromosuccinimide as the brominating agent giving a yield of 43% of trimethylsilyl 3-bromomethyl-7-phenyl-acetamido-3-cephem-4-carboxylate-1-oxide.

EXAMPLE 12

350 mg (1.00 mmole) of 3-methyl-7-phenylacetamido-3-cephem-4-carboxylic acid-1-oxide were silylated with 315 mg 1.54 mmoles) of N,N'-bis(trimethylsilyl)urea as described in Example 11. After cooling in an ice-bath and diluting the reaction mixture to 40 ml with 1,2-dichloroethane, 0.11 ml (1.70 mmoles) of methanesulfonic acid was added and bromination was carried out as described in Example 11 using 290 mg (1.63 mmoles) of N-bromosuccinimide as the brominating agent to obtain a yield of 43% of trimethylsilyl 3-bromomethyl-7-phenyl-acetamido-3-cephem-4-carboxylate-1-oxide.

EXAMPLE 13

370 mg (1.06 mmoles) of 3-methyl-7-phenylacetamido-3-cephem-4-carboxylic acid-1-oxide were silylated with 303 mg (1.48 mmoles) of N,N'-bis(trimethylsilyl)urea in 40 ml of 1,2-dichloroethane by stirring under nitrogen at 30° C. for 1½ hours. The slightly yellow solution obtained was cooled in an ice-bath and 0.98 ml of methanesulfonic acid (1.50 mmoles) was added to it. Bromination was carried out in ¾ hour using 230 mg (0.80 mmole) of 1,3-dibromo-5,5-dimethylhydantoin as the brominating agent to obtain a 45% yield of trimethylsilyl 3-bromomethyl-7-phenylacetamido-3-cephem-4-carboxylate-1-oxide.

EXAMPLE 14

363 mg (1.04 mmoles) of 3-methyl-7-phenylacetamido-3-cephem-4-carboxylic acid-1-oxide were suspended in 20 ml of 1,2-dichloroethane and 304 mg of N,N'-bis (trimethylsilyl)urea (1.49 mmoles) were added thereto. The mixture was stirred under nitrogen at 25° C. for 3 hours and 20 ml of 1,2-dichloroethane were added to the slightly turbid solution. The mixture was cooled in an ice-bath and 0.98 ml (1.50 mmoles) of methanesulfonic acid was added. Bromination was carried out in half an hour using 360 mg (1.59 mmoles) of N-bromophthalimide as the brominating agent to obtain a 48% yield of trimethylsilyl 3-bromomethyl-7-phenylacetamido-3-cephem-4-carboxylate-1-oxide.

EXAMPLE 15

To a suspension of 351 mg (1.01 mmoles) of 3-methyl-7-phenylacetamido-3-cephem-4-carboxylic acid-1-oxide in 20 ml of dichloromethane, 600 mg of diethyl trimethylsilyl trimethylsilylphosphorimidate (2.2 mmoles) were added and after stirring for half an hour at room temperature, a clear solution was obtained. 210 mg of amidosulfonic acid (2.2 mmoles) were added thereto and the volume of the solution was brought to 40 ml by the addition of dichloromethane. The solution was cooled in an ice-bath after which bromination was carried out in one hour using 320 mg (1.80 mmoles) of N-bromosuccinimide as the brominating agent. The yield of trimethylsilyl 3-bromomethyl-7-phenylacetamido-3-cephem-4-carboxylate-1-oxide was 52%.

EXAMPLE 16

A mixture of 349 ml (1.00 mmole) of 3-methyl-7-phenyl-acetamido-3-cephem-4-carboxylic acid-1-oxide, 10 ml of 1,2-dichloroethane and 0.15 ml (0.6 mmole) of N,O-bis(trimethylsilyl)-acetamide was stirred at room temperature under nitrogen for 1¾ hours, after which a clear, yellow solution was obtained. Then, 112 mg (1.15 mmoles) of amidosulfonic acid and 30 ml of 1,2-dichloroethane were added thereto and the mixture obtained was cooled in an ice-bath. Bromination was carried out over one hour using 328 mg (1.84 mmoles) of N-bromosuccinimide as the brominating agent to obtain a yield of 48% of trimethylsilyl 3-bromomethyl-7-phenylacetamido-3-cephem-4-carboxylate-1-oxide.

EXAMPLE 17

152 mg (0.75 mmole) of N,O-bis-(trimethylsilyl)-acetamide were added to a suspension of 370 mg (1.06 mmoles) of 3-methyl-7-phenylacetamido-3-cephem-4-carboxylic acid-1-oxide in 25 ml of refluxing dichloromethane the clear solution that was obtained after refluxing for ¼ hour was diluted to 40 ml with dichloromethane and cooled in an ice-bath. Bromination was carried out over ½ hour with 310 mg (1.74 mmoles) of N-bromosuccinimide as the brominating agent to obtain a yield of 48% of trimethylsilyl 3-bromomethyl-7-phenylacetamido-3-cephem-4-carboxylate-1-oxide.

EXAMPLE 18

To a suspension of 360 mg of 3-methyl-7-phenylacetamido-3-cephem-4-carboxylic acid-1-oxide (1.03 mmoles) in 25 ml of dichloromethane, 187 mg of N,O-bis(trimethylsily) trifluoroacetamide (0.73 mmole) were added and the mixture was refluxed for 2 hours. The clear solution obtained was diluted with dichloromethane to 40 ml and 200 mg (2.04 mmoles) of amidosulfonic acid were added thereto to produce some precipitate. The mixture was cooled in an ice-bath and brominated with 262 mg (1.47 mmoles) of N-bromosuccinimide by irradiating the mixture for 30 minutes to obtain a yield of 44% of trimethylsilyl 3-bromomethyl-7-phenylacetamido-3-cephem-4-carboxylate-1-oxide.

EXAMPLE 19

A mixture of 409 mg (1.18 mmoles) of 3-methyl-7-phenylacetamido-3-cephem-4-carboxylic acid-1-oxide in 25 ml of dichloromethane was silylated with 354 mg (1.78 mmoles) of N-methyl-N-trimethylsilyl-trifluoroacetamido by stirring at room temperature for 45 minutes.

50 mg of amidosulfonic acid (0.51 mmole) were added thereto and the mixture was cooled in an ice-bath. Bromination was carried out in half an hour using 292 mg of N-bromosuccinimide (1.64 mmoles) as the brominating agent to obtain a yield of 49% of trimethylsilyl 3-bromomethyl-7-phenylacetamido-3-cephem-4-carboxylate-1-oxide.

EXAMPLE 20

By stirring a mixture of 361 mg (1.03 mmoles) of 3-methyl-7-phenylacetamido-3-cephem-4-carboxylic acid-1-oxide and 208 mg (1.43 mmoles) of N-methyl-N-trimethylsilylacetamide in 25 ml of dichloromethane for one hour at room temperature, a clear solution was obtained and 150 mg of amidosulfonic acid (1.53 mmoles) were added thereto. The volume of the mixture was brought to about 40 ml by the addition of dichloromethane. The mixture was cooled in an ice-bath and bromination was carried out in half an hour using 280 mg of N-bromosuccinimide (1.57 mmoles) as the brominating agent to obtain a 48% yield of trimethylsilyl 3-bromoethyl-7-phenylacetamido-3-cephem-4-carboxylate-1-oxide.

EXAMPLE 21

366 mg (1.05 mmoles) of 3-methyl-7-phenylacetamido-3-cephem-4-carboxylic acid-1-oxide were silylated in one hour at room temperature by stirring in 25 ml of dichloromethane with 208 mg (1.43 mmoles) of N-methyl-N-trimethylsilylacetamide. The clear solution obtained was cooled in an ice-bath and bromination was carried out in half an hour using 282 mg (1.58 mmoles) of N-bromosuccinimide as the brominating agent to obtain a 44% yield of trimethylsilyl 3-bromomethyl-7-phenylacetamido-3-cephem-4-carboxylate-1-oxide.

EXAMPLE 22

A mixture consisting of 397 mg (1.14 mmoles) of 3-methyl-7-phenylacetamido-3-cephem-4-carboxylic acid-1-oxide, 243 mg (1.28 mmoles) of N,N-bis(trimethylsilyl)formamide and 25 ml of dichloromethane was refluxed for 2½ hours after which a yellow, clear solution was obtained. 15 ml of dichloromethane and 250 mg of amidosulfonic acid (2.6 mmoles) were added to the mixture which was cooled in an ice-bath. Bromination was carried out in half an hour using 360 mg (1.71 mmoles) of N-bromosuccinimide as the brominating agent to obtain a 49% yield of trimethylsilyl 3-bromomethyl-7-phenylacetamido-3-cephem-4-carboxylate-1-oxide.

EXAMPLE 23

To a refluxing suspension of 359 mg (1.03 mmoles) of 3-methyl-7-phenylacetamido-3-cephem-4-carboxylic acid-1-oxide in 25 ml of dichloromethane, 189 mg of N-trimethylsilylacetamide (1.45 mmoles) were added and the clear solution that was obtained after refluxing for ¾ hours was cooled in an ice-bath and diluted to 40 ml with dichloromethane. Bromination was carried out in half an hour using 287 mg (1.61 mmoles) of N-bromosuccinimide as the brominating agent to obtain a yield of 46% of trimethylsilyl 3-bromomethyl-7-phenylacetamido-3-cephem-4-carboxylate-1-oxide.

EXAMPLE 24

342 mg (0.98 mmole) of 3-methyl-7-phenylacetamido-3-cephem-4-carboxylic acid-1-oxide were suspended in 25 ml of dichloromethane and the mixture was heated to reflux 157 mg of N-trimethylsilylacetamide (1.20 mmoles) were added thereto and refluxing was continued for ¾ hour. To the clear, colorless solution obtained, 50 mg of amidosulfonic acid (0.51 mmoles) were added and the mixture was diluted to 40 ml with dichloromethane. The ice-cooled solution was brominated in half an hour using 280 mg (1.57 mmoles) of N-bromosuccinimide as the brominating agent to obtain a yield of 49% of trimethylsilyl 3-bromomethyl-7-phenylacetamido-3-cephem-4-carboxylic acid-1-oxide.

EXAMPLE 25

To a refluxing suspension of 329 mg (0.95 mmole) of 3-methyl-7-phenylacetamido-3-cephem-4-carboxylic acid-1-oxide in 25 ml of dichloromethane, 298 mg (2.27 mmoles) of N-trimethylsilylacetamide were added and a clear, colorless solution was obtained after 15 minutes. Refluxing was continued for another 30 minutes after which 300 mg (3.06 mmoles) of amidosulfonic acid were added. The mixture was diluted with dichloromethane to 40 ml and cooled in an ice-bath. Bromination was carried out in one hour using 280 mg (1.57 mmoles) of N-bromosuccinimide as the brominating agent to obtain a yield of 50% of trimethylsilyl 3-bromomethyl-7-phenylacetamido-3-cephem-4-carboxylate-1-oxide.

EXAMPLE 26

To a suspension of 363 mg of 3-methyl-7-phenylacetamido-3-cephem-4-carboxylic acid-1-oxide (1.04 mmoles) in 25 ml of dichloromethane, 59 mg of bis(trimethylsilyl)sulfate (0.25 mmole) and 78 mg of hexamethyldisilazane (0.48 mmole) were added at room temperature. A clear solution was obtained within ten minutes and was diluted with dichloromethane to 40 ml and cooled in an ice-bath. 100 mg of amidosulfonic acid (1.02 mmoles) were added thereto and bromination was carried out in half an hour using 302 mg of N-bromosuccinimide (1.70 mmoles) as the brominating agent to obtain trimethylsilyl 3-bromomethyl-7-phenylacetamido-3-cephem-4-carboxylate-1-oxide in a 42% yield.

EXAMPLE 27

255 mg of N-trimethylsilylcaprolactam (1.36 mmoles) were added to a refluxing suspension of 360 mg (1.03 mmoles) of 3-methyl-7-phenylacetamido-3-cephem-4-carboxylic acid-1-oxide in 25 ml of dichloromethane and a clear, colorless solution was obtained within 2 minutes. Refluxing was continued for another 25 minutes and the solution was cooled in an ice-bath and diluted to 40 ml with dichloromethane 150 mg of amidosulfonic acid (1.53 mmoles) were added thereto and bromination was carried out in half an hour using 299 mg (1.68 mmoles) of N-bromosuccinimide as the brominating agent to obtain a 51% yield of trimethylsilyl 3-bromomethyl-7-phenylacetamido-3-cephem-4-carboxylate-1-oxide.

EXAMPLE 28

To a refluxing suspension of 404.3 mg (1.16 mmoles) of 3-methyl-7-phenylacetamido-3-cephem-4-carboxylic-1-oxide in 40 ml of dichloromethane, 426.1 mg of N-trimethylsilylphthalimide (1.95 mmoles) were added and a clear, pale yellow solution was obtained after one hour. The solution was cooled in an ice-bath and 329.6 mg (1.85 mmoles) of N-bromosuccinimide were added to it. The mixture was irradiated for half an hour and some precipitate had formed after that period of time. The yield of trimethylsilyl 3-bromomethyl-7-phenylacetamido-3-cephem-4-carboxylate-1-oxide was 46%.

EXAMPLE 29

To a refluxing suspension of 445.2 mg (1.28 mmoles) of 3-methyl-7-phenyl-acetamido-3-cephem-4-carboxylic acid-1-oxide in 40 ml of dichloromethane, 333.4 mg of N-trimethylsilylsuccinimide (1.95 mmoles) were added and after 10 minutes, a clear solution was obtained. This was cooled in an ice-bath and brominated in half an hour with 318.5 mg (1.79 mmoles) of N-bromosuccinimide to obtain a 48% yield of trimethylsilyl 3-bromomethyl-7-phenylacetamido-3-cephem-4-carboxylate-1-oxide.

EXAMPLE 30

A clear solution was obtained after refluxing a suspension of 371.8 mg (1.07 mmoles) of 3-methyl-7- phenylacetamido-3-cephem-4-carboxylic acid-1-oxide and 284.7 mg (1.65 mmoles) of N-trimethylsilyldiacetamide in 40 ml of dichloromethane for 5 minutes and it was cooled in an ice-bath and brominated in half an hour with 290.2 mg (1.63 mmoles) of N-bromosuccinimide to obtain a 47% yield of trimethylsilyl 3-bromomethyl-7-phenylacetamido-3-cephem-4-carboxylate-1-oxide.

EXAMPLE 31

To a refluxing suspension of 347 mg (1.00 mmole) of 3-methyl-7-phenylacetamido-3-cephem-4-carboxylic acid-1-oxide in 25 ml of dichloromethane, 340 mg of N-trimethylsilylhexahydrophthalimide (1.5 mmoles) were added and after refluxing for 50 minutes, a second portion of 340 mg of N-trimethylsilylhexahydrophthalimide (1.5 mmoles) was added thereto. The clear solution that was obtained after refluxing for ten minutes was diluted with dichloromethane to approximately 40 ml, was cooled in an ice-bath and then bromination was carried out in one hour using 260 mg (1.46 mmoles) of N-bromosuccinimide as the brominating agent to obtain a 45% yield of of trimethylsilyl 3-bromomethyl-7-phenylacetamido-3-cephem-4-carboxylate-1-oxide.

EXAMPLE 32

To a refluxing suspension of 359 mg (1.03 mmoles) of 3-methyl-7-phenylacetamido-3-cephem-4-carboxylic acid-1-oxide in 25 ml of dichloromethane, 151 mg (0.48 mmole) of trimethylsilyl bis(trimethylsilyl)amidosulfonate were added and refluxing was continued for 2 hours. The solution obtained was diluted to 40 ml with dichloromethane and cooled in an ice-bath. Bromination was carried out in half an hour using 290 mg (1.67 mmoles) of N-bromosuccinimide as the brominating agent to obtain a 45% yield of trimethylsilyl 3-bromomethyl-7-phenylacetamido-3-cephem-4-carboxylate-1-oxide.

EXAMPLE 33

367 mg (1.05 mmoles) of 3-methyl-7-phenylacetamido-3-cephem-4-carboxylic acid-1-oxide were suspended in 25 ml of dichloromethane and the mixture was heated to reflux, 85 mg of hexamethyldisilazane (0.53 mmole) were added thereto and after refluxing for 2 hours, 36 mg of trimethylsilyl trimethylsilylamidosulfonate (0.15 mmole) were added. Refluxing was continued for two hours more and the slightly turbid solution obtained was cooled in an ice-bath and bromination was carried out in half an hour using 277 mg (1.56 mmoles) of N-bromosuccinimide as the brominating agent to obtain a yield of 49% of trimethylsilyl 3-bromomethyl-7-phenylacetamido-3-cephem-4-carboxylate-1-oxide.

EXAMPLE 34

A mixture consisting of 421 mg (1.21 mmoles) of 3-methyl-7-phenylacetamido-3-cephem-4-carboxylic acid-1-oxide, 97.6 mg (0.60 mmole) of hexamethyldisilazane and 88.2 mg (0.47 mmole) of N-trimethylsilylcaprolactam in 25 ml of dichloromethane was refluxed for one hour and the clear solution obtained was diluted to 40 ml with dichloromethane and cooled in an ice-bath. Bromination was carried out in half an hour using 345 mg (1.94 mmoles) of N-bromosuccinimide as the brominating agent to obtain a yield of 45% of trimethylsilyl 3-bromomethyl-7-phenylacetamido-3-cephem-4-carboxylate-1-oxide.

EXAMPLE 35

To a refluxing suspension of 375 mg (1.08 mmoles) of 3-methyl-7-phenylacetamido-3-cephem-4-carboxylic acid-1-oxide in 25 ml of dichloromethane, 87 mg (0.54 mmole) of hexamethyldisilazane and 80 mg (0.43 mmole) of N-trimethylsilylcaprolactam were added. The clear solution that was obtained after refluxing for ¾ hour was refluxed for half an hour more, was diluted with dichloromethane to approximately 40 ml and 10 mg of trifluoroacetic acid (0.09 mmole) were added to it. The solution was cooled in an ice-bath and brominated with 310 mg (1.74 mmoles) of N-bromosuccinimide in half an hour to obtain a 48% yield of trimethylsilyl 3-bromomethyl-7-phenylacetamido-3-cephem-4-carboxylate-1-oxide.

EXAMPLE 36

To a solution of 0.78 g (2.87 mmoles) of 1,3-bis(trimethylsilyl)-5,5-dimethylhydantoin in 25 ml of dichloromethane, 0.70 g (2 mmoles) of 3-methyl-7-phenylacetamido-3-cephem-4-carboxylic acid-1-oxide were added and the mixture was refluxed for half an hour. The clear pale yellow solution obtained was diluted to approximately 50 ml with dichloromethane and cooled in an ice-bath. Bromination was carried out in half an hour using 0.57 mg (3.2 mmoles) of N-bromosuccinimide as the brominating agent to obtain a 45% yield of trimethylsilyl 3-bromomethyl-7-phenylacetamido-3-cephem-4-carboxylate-1-oxide.

EXAMPLE 37

To a suspension of 350 mg (1 mmole) of 3-methyl-7-phenylacetamido-3-cephem-4-carboxylic acid-1-oxide in 40 ml of chlorobenzene, 0.3 ml of N-methyl-N-trimethylsilyltrifluoroacetamide (1.6 mmoles) was added and the mixture was stirred at room temperature for one hour. The silyl ester obtained was poorly soluble in the solvent at lower temperatures and the bromination with 290 mg (1.63 mmoles) of N-bromosuccinimide was therefore started at room temperature, but the mixture was cooled to 0° C. in the course of 15 minutes. After irradiation for half an hour, the bromination was completed for a 43% yield of trimethylsilyl 3-bromomethyl-7-phenylacetamido-3-cephem-4-carboxylate-1-oxide.

EXAMPLE 38

0.3 ml of N-methyl-N-trimethylsilyltrifluoroacetamide (1.6 mmoles) was added at room temperature to a suspension of 354 mg (1.02 mmoles) of 3-methyl-7-phenylacetamido-3-cephem-4-carboxylic acid-1-oxide in 40 ml of o-dichlorobenzene and after stirring for 15 minutes, 20 ml of o-dichlorobenzene were added thereto. Bromination was carried out as described in Example 37 using 310 mg (1.74 mmoles) of N-bromosuccinimide as the brominating agent and irradiation was continued for 80 minutes to obtain trimethylsilyl 3-bromomethyl-7-phenylacetamido-3-cephem-4-carboxylate-1-oxide in a yield of 45%.

EXAMPLE 39

358 mg (1.03 mmoles) of 3-methyl-7-phenylacetamido-3-cephem-4-carboxylic acid-1-oxide and 420 mg (1.67 mmoles) of trimethylsilyl trimethylsilylamidosulfonate were added to 40 ml of ethyl acetate and the mixture was stirred at 40° C. for ¾ hour. The clear solution obtained was cooled to room temperature and bromination was carried out in half an hour using 290 mg (1.63 mmoles) of N-bromosuccinimide as the brominating agent to obtain trimethylsilyl 3-bromomethyl-7-phenylacetamido-3-cephem-4-carboxylate-1-oxide in a yield of 57%.

EXAMPLE 40

A mixture consisting of 349 mg (1.00 mmole) of 3-methyl-7-phenylacetamido-3-cephem-4-carboxylic acid-1-oxide, 420 mg (1.67 mmoles) of trimethylsilyl trimethylsilylamidosulfonate and 40 ml of ethyl formate was stirred at 40° C. for ¾ hour after which a clear solution containing a heavy precipitate was obtained. This was cooled to room temperature and 290 mg (1.63 mmoles) of N-bromosuccinimide were added to it. After irradiation for 5 minutes, the mixture was cooled in an ice-bath and irradiation was continued for 25 minutes to obtain a yield of 52% of trimethylsilyl 3-bromomethyl-7-phenylacetamido-3-cephem-4-carboxylate-1-oxide.

EXAMPLE 41

To a suspension of 355 mg (1.02 mmoles) of 3-methyl-7-phenylacetamido-3-cephem-4-carboxylic acid-1-oxide in 10 ml of 1,2-dichloroethane kept at a temperature of 40° C., 0.15 ml (0.72 mmole) of hexamethyldisilazane was added. After stirring at that temperature for 2 hours, a clear solution was obtained to which 30 ml of 1,2-dichloroethane were added. The solution was cooled in an ice-bath and bromination was carried out in half an hour using 293 mg (1.65 mmoles) of N-bromosuccinimide as the brominating agent to obtain a yield of 42% of trimethylsilyl 3-bromomethyl-7-phenylacetamido-3-cephem-4-carboxylate-1-oxide.

EXAMPLE 42

403 mg (1.16 mmoles) of 3-methyl-7-phenylacetamido-3-cephem-4-carboxylic acid-1-oxide were silylated in 25 ml of dichloromethane with 1.26 mg (0.78 mmole) of hexamethyldisilazane by refluxing for 3 hours. The solution obtained was diluted with dichloromethane to 40 ml and cooled in an ice-bath. Bromination was carried out in half an hour using 266 mg (0.93 mmole) of 1,3-dibromo-5,5-dimethylhydantoin as the brominating agent to obtain a yield of 42% of trimethylsilyl 3-bromomethyl-7-phenylacetamido-3-cephem-4-carboxylte-1-oxide.

EXAMPLE 43

A mixture consisting of 394 mg (1.08 mmoles) of 3-methyl-7-phenoxyacetamido-3-cephem-4-carboxylic acid-1-oxide and 208 mg (0.86 mmole) of trimethylsilyl trimethylsilylamidosulfonate in 25 ml of dichloromethane was refluxed for 2 hours and the transluent suspension obtained was cooled in an ice-bath and diluted with dichloromethane to about 40 ml. Bromination was carried out in half an hour using 289 mg (1.62 mmoles) of N-bromosuccinimide as the brominating agent to obtain a 41% yield of trimethylsilyl 3-bromomethyl-7-phenyloxyacetamido-3-cephem-4-carboxylate-1-oxide.

EXAMPLE 44

374 mg (1.03 mmoles) of 3-methyl-7-phenoxyacetamido-3-cephem-4-carboxylic acid-1-oxide were silylated with 159 mg (0.78 mmole) of trimethylsilyl trimethylsilylcarbamate by refluxing in 25 ml of dichloromethane for 4 hours. 150 mg (1.53 mmoles) of amidosulfonic acid were added thereto and the solution was diluted to 40 ml with dichloromethane, was cooled in an ice-bath and bromination was carried out with 261 mg (1.46 mmoles) of N-bromosuccinimide in half an hour. The yield of trimethylsilyl 3-bromomethyl-7-phenoxyacetamido-3-cephem-4-carboxylate-1-oxide was 47%.

EXAMPLE 45

162 mg (1.0 mmole) of hexamethyldisilazane and 5.4 mg (0.08 mmole) of imidazole were added at reflux to a suspension of 396.6 mg (1.54 mmoles) of 7-formamido-3-methyl-3-cephem-4-carboxylic acid-1-oxide in 40 ml of dichloromethane and after refluxing for ¾ hour, a clear, faintly yellow solution was obtained. 100 mg of amidosulfonic acid (1.02 mmoles) were added thereto and the mixture was stirred for half an hour at room temperature. After cooling in an ice-bath, bromination was carried out by adding 336.2 mg (1.89 mmoles) of N-bromosuccinimide. After irradiation for one hour, another portion of 100 mg of N-bromosuccinimide (0.56 mmoles) was added and irradiation was continued for half an hour more to obtain a 58% yield of trimethylsilyl 3-bromomethyl-7-formamido-3-cephem-4-carboxylate-1-oxide.

EXAMPLE 46

325 mg (1.63 mmoles) of N-methyl-N-trimethylsilyl-trifluoroacetamide were added at room temperature to a suspension of 280.7 mg (1.09 mmoles) of 7-formamido-3-methyl-3-cephem-4-carboxylic acid-1-oxide in 40 ml of dichloromethane and the mixture was stirred for half an hour, after which an almost clear solution was obtained. This was cooled in an ice-bath and 69.5 mg (0.71 mmole) of amidosulfonic acid were added to it. Bromination was carried out in half an hour using 275.8 mg (1.55 mmoles) of N-bromosuccinimide as the brominating agent to obtain a 52% yield of trimethylsilyl 3-bromomethyl-7-formamido-3-cephem-4-carboxylate-1-oxide.

EXAMPLE 47

241 mg of trimethylsilyl trimethylsilylcarbamate (1.18 mmoles) were added to a refluxing suspension of 312 mg (1.21 mmoles) of 7-formamido-3-methyl-3-cephem-4-carboxylic acid-1-oxide in 25 ml of dichloromethane and reflux was continued for 4 hours.

150 mg of amidosulfonic acid (1.53 mmoles) and 15 ml of dichloromethane were added to the solution obtained and the mixture was cooled in an ice-bath. Bromination was carried out in one hour using 269 mg (1.51 mmoles) of N-bromosuccinimide as the brominating agent to obtain a 49% yield of trimethylsilyl 3-bromomethyl-7-formamido-3-cephem-4-carboxylate-1-oxide.

EXAMPLE 48

To a refluxing mixture of 317 mg (1.23 mmoles) of 7-formamido-3-methyl-3-cephem-4-carboxylic acid-1-oxide in 25 ml of dichloromethane were added 71.4 mg (0.30 mmoles) of bis-(trimethylsilyl)-sulfate and B 91.6 mg (0.57 mmole) of hexamethyldisilazane to obtain a clear, colorless solution after 15 minutes. This solution was stirred for 2 hours and dichloromethane was added to dilute the solution to 40 ml. The solution was then cooled in an ice-bath and brominated in half an hour with 246 mg (1.38 mmoles) of N-bromosuccinimide to obtain a 50% yield of trimethylsilyl 3-bromomethyl-7-formamido-3-cephem-4-carboxylate-1-oxide.

EXAMPLE 49

A suspension of 357.6 mg (1.39 mmoles) of 7-formamido-3-methyl-3-cephem-4-carboxylic acid-1-oxide in 40 ml of dichloromethane was heated to reflux and 359 mg (1.94 mmoles) of N-trimethylsilylcaprolactam were added thereto to obtain a clear, colorless solution within 3 minutes. This was cooled in an ice-bath and 100 mg (1.02 mmoles) of amidosulfonic acid were added. Bromination was carried out in half an hour using 301.3 mg (1.69 mmoles) of N-bromosuccinimide as the brominating agent to obtain a 62% yield of trimethylsilyl 3-bromomethyl-7-formamido-3-cephem-4-carboxylate-1-oxide.

EXAMPLE 50

114 mg (0.71 mmole) of hexamethyldisilazane were added to a refluxing suspension of 348 mg (1.04 mmoles) of 7-benzamido-3-methyl-3-cephem-4-carboxylic acid-1-oxide in 25 ml of dichloromethane and reflux was continued for 2 hours. The clear, slightly colored solution was diluted with dichloromethane to approximately 40 ml and 50 mg of amidosulfonic acid (0.51 mmole) were added thereto. The solution was cooled in an ice-bath and, bromination was carried out in half an hour using 296 mg of N-bromosuccinimide (1.66 mmoles) as the brominating agent to obtain a yield of 55% of trimethylsilyl 7-benzamido-3-bromomethyl-3-cephem-4-carboxylate-1-oxide.

EXAMPLE 51

339 mg (1.02 mmoles) of 7-benzamido-3-methyl-3-cephem-4-carboxylic acid-1-oxide were silylated as described in Example 50. After dilution to 40 ml, 5 mg of methanesulfonic acid (0.05 mmoles) were added thereto and the mixture was cooled in an ice-bath. Bromination was carried out in half an hour using N-bromosuccinimide (289 mg 1.62 mmoles) as the brominating agent to obtain a 57% yield of trimethylsilyl 7-benzamido-3-bromomethyl-3-cephem-4-carboxylate-1-oxide.

EXAMPLE 52

207 mg (0.86 mmoles) of trimethylsilyl trimethylsilylamidosulfonate were added to a suspension of 353 mg (1.06 mmoles) of 7-benzamido-3-methyl-3-cephem-4-carboxylic acid-1-oxide in 25 ml of dichloromethane and the mixture was stirred at 40° C. for 3 hours. The colorless translucent suspension was cooled in an ice-bath and bromination was carried out in half an hour using 277 mg of N-bromosuccinimide (1.56 mmoles) as the brominating agent to obtain a 49% yield of trimethylsilyl 7-benzamido-3-bromomethyl-3-cephem-4-carboxylate-1-oxide.

EXAMPLE 53

To a suspension of 335 mg (1.00 mmole) of 7-benzamido-3-methyl-3-cephem-4-carboxylic acid-1-oxide in 25 ml of dichloromethane, 279 mg of N-methyl-N-trimethylsilyltrifluoroacetamide (1.40 mmoles) were added and the mixture was stirred for 10 minutes at room temperature to obtain a clear, yellow solution. This was cooled in an ice-bath and bromination was carried out in half an hour using 253 mg of N-bromosuccinimide (1.42 mmoles) as the brominating agent to obtain a yield of 52% of trimethylsilyl 7-benzamido-3-bromomethyl-3-cephem-4-carboxylate-1-oxide.

EXAMPLE 54

324 mg (1.63 mmoles) of N-methyl-N-trimethylsilyltrifluoroacetamide were added to a suspension of 409 mg (1.22 mmoles) of 7-benzamido-3-methyl-3-cephem-4-carboxylic acid-1-oxide in 25 ml of dichloromethane and after stirring at room temperature for 10 minutes, a clear, slightly yellow solution was obtained. This was diluted to 40 ml with dicloromethane and 50 mg of amidosulfonic acid (0.51 mmole) were added. This solution was cooled in an ice-bath and was brominated in one hour with 301 mg (1.70 mmoles) of N-bromosuccinimide to obtain a yield of 59% of trimethylsilyl 7-benzamido-3-bromomethyl-3-cephem-4-carboxylate-1-oxide.

EXAMPLE 55

60.4 mg of bis(trimethylsilyl)sulfate (0.25 mmole) and 80.3 mg of hexamethyldisilazane (0.50 mmole) were added to a suspension of 357.0 (1.07 mmoles) of 7-benzamido-3-methyl-3-cephem-4-carboxylic acid-1-oxide in 25 ml of dichloromethane and a clear solution was obtained after stirring for 5 minutes at room temperature. After diluting to 40 ml with dichloromethane and cooling in an ice-bath, bromination was carried out in half an hour using 295 mg (1.66 mmoles) of N-bromosuccinimide as the brominating agent to obtain a 60% yield of trimethylsilyl 7-benzamido-3-bromomethyl-3-cephem-4-carboxylate-1-oxide.

EXAMPLE 56

208 mg of N-trimethylsilylacetamide (1.59 mmoles) were added to a suspension of 383 mg (1.14 mmoles) of 7-benzamido-3-methyl-3-cephem-4-carboxylic acid-1-oxide in 25 ml of dichloromethane, and after stirring for 1½ hours at room temperature, a clear solution was obtained, which was diluted with dichloromethane to 50 ml. 200 mg of amidosulfonic acid (1.04 mmoles) were added thereto and the mixture was cooled in an ice-bath. Bromination was carried out in half an hour using 310 mg (1.74 mmoles) of N-bromosuccinimide as the brominating agent to obtain a 48% yield of trimethylsilyl 7-benzamido-3-bromomethyl-3-cephem-4-carboxylate-1-oxide.

EXAMPLE 57

152 mg (0.74 mmoles) of trimethylsilyl trimethylsilycarbamate were added to a suspension of 349 mg (1.04 mmoles) of 7-benzamido-3-methyl-3-cephem-4-carboxylic acid-1-oxide in 25 ml of dichloromethane which was heated to reflux, and a clear solution was obtained after 4 hours of refluxing. The solution was diluted to approximately 50 ml with dichloromethane and cooled in an ice-bath. 100 mg of amidosulfonic acid (1.02 mmoles) were added thereto and bromination was carried out in half an hour using 291 mg (1.63 mmoles) of N-bromosuccinimide as the brominating agent to obtain a 55% yield of trimethylsilyl 7-benzamido-3-bromomethyl-3-cephem-4-carboxylate-1-oxide.

EXAMPLE 58

125 mg of hexamethyldisilazane (0.78 mmoles) were added to a warm (40° C.) suspension of 353.3 mg (1.06 mmoles) of 7-benzamido-3-methyl-3-cephem-4-carboxylic acid-1-oxide in 40 ml of dichloromethane and the mixture obtained was stirred at that temperature for 2½ hours. The clear, light yellow solution was cooled in an ice-bath and 70 mg of 10-camphorsulfonic acid (0.30 mmoles) were added thereto. Bromination was carried out in 50 minutes, using 287 mg of N-bromosuccinimide (1.61 mmoles) as the brominating agent to obtain a 45% yield of trimethylsilyl 7-benzamido-3-bromomethyl-3-cephem-4-carboxylate-1-oxide.

EXAMPLES 59–68

7-benzamido-3-methyl-3-cephem-4-carboxylic acid-1-oxide (II) was silylated in 50 ml of refluxing dichloromethane with hexamethyldislazane. The solution of the trimethylsilyl ester was cooled in an ice-bath and a quantity of an acid was added. Bromination was carried out with N-bromosuccinimide by irradiation with a 150 W tungsten lamp for half an hour. Further details are to be found in Table II.

were silylated by stirring at 30° C. for 1.5 hours in 60 ml of 1,2-dichloroethane with 1.0 g (4.3 mmoles) of N-trimethylsilyltrichloroacetamide. The slightly yellow, substantially clear solution obtained was cooled in an ice-bath and bromination was carried out in 15 minutes using 250 mg (0.87 mmole) of 1,3-dibromo-5,5-dimethylhydantoin as the brominating agent. During the bromination reaction, the mixture was irradiated with a 520 W fluorescent lamp to obtain a 48% yield of trimethylsilyl 3-bromomethyl-7-phenylacetamido-3-cephem-4-carboxylate-1-oxide.

EXAMPLE 72

458 mg of 3-methyl-7-phenylacetamido-3-cephem-4-carboxylic acid-1-oxide (1.32 mmoles) were silylated in

TABLE II

| Example | mmoles of II | mmole of HMDS | time of silylation (h) | acid added (mmole) | mmoles of NBS | Yield % |
|---|---|---|---|---|---|---|
| 59 | 1.32 | 0.88 | 1.5 | 4-ClC$_6$H$_4$SO$_3$H (0.22) | 1.88 | 61 |
| 60 | 1.20 | 0.82 | 1.5 | HCOOH (0.21) | 1.78 | 61 |
| 61 | 1.35 | 0.92 | 2.5 | BrCH$_2$COOH (0.15) | 1.97 | 49 |
| 62 | 1.22 | 0.83 | 2.5 | 4-CH$_3$C$_6$H$_4$SO$_3$H (0.20) | 1.78 | 59 |
| 63 | 1.40 | 0.92 | 2.0 | 2-ClC$_6$H$_4$COOH (0.15) | 2.04 | 51 |
| 64 | 1.34 | 0.89 | 2.0 | 4-NO$_2$C$_6$H$_4$COOH (0.15) | 1.96 | 54 |
| 65 | 1.16 | 0.80 | 3.0 | 4-NO$_2$C$_6$H$_4$CH$_2$COOH (0.15) | 1.70 | 52 |
| 66 | 1.33 | 0.88 | 3.0 | C$_6$H$_5$CHClCOOH (0.15) | 1.94 | 53 |
| 67 | 1.01 | 0.70 | 1.5 | H$_2$SO$_4$ (0.05) | 1.57 | 44 |
| 68 | 1.02 | 0.70 | 1.5 | HCl (0.04) | 1.57 | 51 |

EXAMPLE 69

A mixture consisting of 400.5 mg (1.20 mmoles) of 7-benzamido-3-methyl-3-cephem-4-carboxylic acid-1-oxide, 0.69 g (4.3 mmoles) of N-trimethylsilylurethane and 20 mg of bis-(trimethylsilyl)-sulfate in 40 ml of dichloromethane was refluxed for ¾ hours after which a clear solution was obtained. This was cooled in an ice-bath and bromination was carried out after the addition of 200 mg (2.04 mmoles) of amidosulfonic acid using 325.3 mg (1.83 mmoles) of N-bromosuccinimide as the brominating agent. The bromination took half an hour to obtain a 65% yield of trimethylsilyl 7-benzamido-3-bromomethyl-3-cephem-4-carboxylate-1-oxide.

EXAMPLE 70

375 mg (1.88 mmoles) of N-methyl-N-trimethylsilyltrifluoroacetamide were added to a suspension of 387.5 mg (1.16 mmoles) of 7-benzamido-3-methyl-3-cephem-4-carboxylic acid-1-oxide in 40 ml of benzene at room temperature and after stirring at room temperature for half an hour, a clear, yellow solution was obtained. This was cooled to 5° C. and bromination was carried out in half an hour with 306.0 mg (1.72 mmoles) of N-bromosuccinimide as the brominating agent to obtain a 56% yield of trimethylsilyl 7-benzamido-3-bromomethyl-3-cephem-4-carboxylate-1-oxide.

EXAMPLE 71

420 mg (1.21 mmoles) of 3-methyl-7-phenylacetamido-3-cephem-4-carboxylic acid-1-oxide 40 ml of dichloromethane with 397 mg (2.06 mmoles) of N-trimethylsilylbenzamide by refluxing for half an hour and the clear, pale yellow solution was cooled in an ice-bath. Bromination was carried out in half an hour with 378.5 mg (2.13 mmoles) of N-bromosuccinimide as the brominating agent to obtain a 42% yield of trimethylsilyl 3-bromomethyl-7-phenylacetamido-3-cephem-4-carboxylate-1-oxide.

EXAMPLE 73

A mixture consisting of 753 mg (2.16 mmoles) of 3-methyl-7-phenylacetamido-3-cephem-4-carboxylic acid-1-oxide, 785 mg (4.94 mmoles) of N-trimethylsilyl-2-oxazolidinone and 70 ml of dichloromethane was refluxed for 2 hours, after which a clear, almost colorless solution was obtained. This was cooled in an ice-bath and bromination was carried out in half an hour using 624.5 mg (3.51 mmoles) of N-bromosuccinimide as the brominating agent to obtain a yield of 48% of trimethylsilyl 3-bromomethyl-7-phenylacetamido-3-cephem-4-carboxylate-1-oxide.

EXAMPLE 74

By refluxing a mixture consisting of 632.4 mg (1.82 mmoles) of 3-methyl-7-phenylacetamido-3-cephem-4-carboxylic acid-1-oxide, 0.58 g (2.4 mmoles) of 1,3-bis-(trimethylsilyl)-hydantoin and 50 ml of dichloromethane for 2 hours, a clear, pale yellow solution was obtained. This was cooled in an ice-bath and bromination was carried out with 0.52 g (2.9 mmoles) of N-bromosuccinimide to obtain a yield of 41% of trimethylsilyl 3-bromomethyl-7-phenylacetamido-3-cephem-4-carboxylate-1-oxide after irradiating the mixture for half an hour.

EXAMPLE 75

263.4 mg of 3-methyl-7-phenylacetamido-3-cephem-4-carboxylic acid-1-oxide (0.76 mmoles) were added to a solution of 256 mg (1.08 mmoles) of N-trimethylsilyl-4-nitrobenzamide in 50 ml of dichloromethane and the clear solution that was obtained after refluxing this mixture for one hour was cooled in an ice-bath. Bromination was carried out in half an hour using 194.4 mg (1.09 mmoles) of N-bromosuccinimide as the brominating agent and some precipitate was formed after 20 minutes irradiation to obtain a 44% yield of trimethylsilyl 3-bromomethyl-7-phenylacetamido-3-cephem-4-carboxylate-1-oxide.

EXAMPLE 76

The clear solution obtained after refluxing a mixture consisting of 389.7 mg (2.25 mmoles) of N-trimethylsilyl-2,2-dimethylpropanamide, 455.8 mg (1.31 mmoles) of 3-methyl-7-phenylacetamido-3-cephem-4-carboxylic acid-1-oxide and 40 ml of dichloromethane for one hour was cooled in an ice-bath. Then, bromination was carried out in half an hour using 332.2 mg (1.87 mmoles) of N-bromosuccinimide as the brominating agent. After irradiation for 20 minutes, some precipitate was formed. The yield of trimethylsilyl 3-bromomethyl-7-phenylacetamido-3-cephem-4-carboxylate-1-oxide was 45%.

EXAMPLE 77

114 mg of hexamethyldisilazane (0.70 mmoles) were added to a refluxing suspension of 351 mg (1.01 mmoles) of 3-methyl-7-phenylacetamido-3-cephem-4-carboxylic acid-1-oxide in 5 ml of dichloromethane. After the addition of 10 ml of benzene, refluxing was continued for 3 hours and the slightly turbid solution obtained was diluted with 10 ml of dichloromethane and 15 ml of benzene. 100 mg of amidosulfonic acid (1.02 mmoles) were added thereto and the mixture was cooled in an ice-bath. Bromination was carried out with 280 mg (1.57 mmoles) of N-bromosuccinimide to obtain a 43% yield of trimethylsilyl 3-bromomethyl-7-phenylacetamido-3-cephem-4-carboxylate-1-oxide after irradiating the mixture for half an hour.

EXAMPLE 78

81.5 mg of hexamethyldisilazane (0.51 mmole) and 62.6 mg of bis-(trimethylsilyl)-sulfate (0.26 mmole) were added to a suspension of 348 mg (1.00 mmole) of 3-methyl-7-phenylacetamido-3-cephem-4-carboxylic acid-1-oxide in 10 ml of dichloromethane and the clear solution which was obtained after refluxing the mixture for 30 minutes was diluted with 25 ml of ethyl acetate and cooled in an ice-bath. Then, bromination was carried out in one hour using 310 mg (1.74 mmoles) of N-bromosuccinimide as the brominating agent to obtain a 40% yield of trimethylsilyl 3-bromomethyl-7-phenylacetamido-3-cephem-4-carboxylate-1-oxide.

EXAMPLE 79

The clear solution that was obtained after stirring a mixture of 350 mg (1.01 mmoles) of 3-methyl-7-phenylacetamido-3-cephem-4-carboxylic acid-1-oxide, 62.8 mg (0.25 mmole) of bis-(trimethylsilyl)-sulfate, 81.7 mg (0.51 mmole) of hexamethyldisilazane and 10 ml of dichloromethane for half an hour at room temperature was diluted with 30 ml of ethyl formate and was cooled in an ice bath. Bromination was carried out in half an hour using 300 mg (1.69 mmoles) of N-bromosuccinimide as the brominating agent and a precipitate was formed during brominating to obtain a 46% yield of trimethylsilyl 3-bromomethyl-7-phenylacetamido-3-cephem-4-carboxylate-1-oxide.

EXAMPLE 80

Nitrogen was bubbled through a suspension of 369 mg (1.06 mmoles) of 3-methyl-7-phenylacetamido-3-cephem-4-carboxylic acid-1-oxide in 25 ml of dry benzene containing 120 mg (0.74 mmoles) of hexamethyldisilazane for 2 hours at 40° C. and to the gel obtained, 30 ml of dichloromethane were added. The mixture was stirred at 40° C. for 2 hours and 100 mg of amidosulfonic acid (1.02 mmoles) were added to the mixture which was cooled to 10° C. Bromination was carried out in 90 minutes using 300 mg (1.70 mmoles) of N-bromosuccinimide as the brominating agent to obtain a 46% yield of trimethylsilyl 3-bromomethyl-7-phenylacetamido-3-cephem-4-carboxylate-1-oxide.

EXAMPLE 81

355.9 mg (2.06 mmoles) of N-trimethylsilyl-2,2-dimethylpropanamide were added to a suspension of 426.0 mg (1.22 mmoles) of 3-methyl-7-phenylacetamido-3-cephem-4-carboxylic acid-1-oxide in a mixture of 40 ml of dichloromethane and 2 ml of nitrobenzene and the mixture obtained was refluxed for one hour. The clear solution obtained was cooled in an ice-bath and bromination was carried out in half an hour using 336.6 mg (1.89 mmoles) of N-bromosuccinimide as the brominating agent to obtain a 44% yield of trimethylsilyl 3-bromomethyl-7-phenylacetamido-3-cephem-4-carboxylate-1-oxide.

EXAMPLE 82

380.7 mg (1.09 mmoles) of 3-methyl-7-phenylacetamido-3-cephem-4-carboxylic acid-1-oxide were silylated by refluxing in 60 ml of dichloromethane with 320.5 mg (1.85 mmoles) of N-trimethylsilyl-2,2-dimethylpropanamide for half an hour. After the addition of 0.1 g (1 mmole) of amidosulfonic acid, the clear, slightly yellow solution was cooled in an ice-bath and bromination was carried out in half an hour using 291.4 mg (1.64 mmoles) of N-bromosuccinimide as the brominating agent to obtain a 44% yield of trimethylsilyl 3-bromomethyl-7-phenylacetamido-3-cephem-4-carboxylate-1-oxide.

EXAMPLE 83

352 mg (1.01 mmoles) of 3-methyl-7-phenylacetamido-3-cephem-4-carboxylic acid-1-oxide were silylated in 40 ml of chloroform at 60° C. in half an hour with 0.28 g (1.8 mmoles) of N-trimethylsilyl-2,2-dimethylpropanamide and the clear, pale yellow solution obtained was cooled in an ice-bath. Bromination was carried out in half an hour using 0.24 g (1.35 mmoles) of N-bromosuccinimide as the brominating agent to obtain a 40% yield of trimethylsilyl 3-bromomethyl-7-phenylacetamido-3-cephem-4-carboxylate-1-oxide.

EXAMPLE 84

The clear solution that was obtained after refluxing a mixture of 357 mg (1.02 mmoles) of 3-methyl-7- phenylacetamido-3-cephem-4-carboxylic acid-1-oxide, 50 ml of chloroform and 2 ml (about 10 mmoles) of N-trimethylsilylsuccinimide for one and a half hours was cooled in an ice-bath. Bromination was carried out in half an hour using 0.24 mg (1.35 mmoles) of N-bromosuccinimide as the brominating agent to obtain a 42% yield of trimethylsilyl 3-bromomethyl-7-phenylacetamido-3-cephem-4-carboxylate-1-oxide.

EXAMPLE 85

0.1 g (1 mmole) of amidosulfonic acid was added to the clear solution obtained after refluxing a mixture of 571.8 mg (1.64 mmoles) of 3-methyl-7-phenylacetamido-3-cephem-4-carboxylic acid-1-oxide, 627.7 mg (2.31 mmoles) of 1,3-bis-(trimethylsilyl)-5,5-dimethylhydantoin and 50 ml of dichloromethane for one hour and the mixture was cooled in an ice-bath. Bromination was carried out in half an hour using 445.5 mg (2.50 mmoles) of N-bromosuccinimide as the brominating agent to obtain a 42% yield of trimethylsilyl 3-bromomethyl-7-phenylacetamido-3-cephem-4-carboxylate-1-oxide.

EXAMPLE 86

601.5 mg (1.73 mmoles) of 3-methyl-7-phenylacetamido-3-cephem-4-carboxylic acid-1-oxide were silylated by refluxing in 50 ml of dichloromethane for one hour with 503 mg (2.61 mmoles) of N-trimethylsilylbenzamide. 0.1 g of amidosulfonic acid (1 mmole) were added to the clear, slightly yellow solution obtained and after cooling in an ice-bath, bromination was carried out in half an hour with 464.8 mg (2.61 mmoles) of N-bromosuccinimide to obtain a yield of 42% of trimethylsilyl 3-bromomethyl-7-phenylacetamido-3-cephem-4-carboxylate-1-oxide.

EXAMPLE 87

The clear solution obtained after refluxing a mixture consisting of 40 ml of dichloromethane, 608.7 mg (1.75 mmoles) of 3-methyl-7-phenylacetamido-3-cephem-4-carboxylic acid-1-oxide and 450 mg (2.83 mmoles) of N-trimethylsilyl-2-oxazolidinone for two hours was cooled in an ice-bath and 0.1 g of amidosulfonic acid (1 mmole) was added thereto. Bromination was carried out in half an hour using 469 mg (2.63 mmoles) of N-bromosuccinimide as the brominating agent to obtain a 46% yield of trimethylsilyl 3-bromomethyl-7-phenylacetamido-3-cephem-4-carboxylate-1-oxide.

EXAMPLE 88

352 mg (1.01 mmoles) of 3-methyl-7-phenylacetamido-3-cephem-4-carboxylic acid-1-oxide were added to a solution of 0.45 mg (2.0 mmoles) of N-trimethylsilylbenzenesulfonamide in 70 ml of dichloromethane and after refluxing for half an hour a still slightly turbid solution was obtained. An additional 0.42 g of N-trimethylsilylbenzenesulfonamide (1.8 mmoles) was added and refluxing was continued for half an hour. The clear, light yellow solution obtained was cooled in an ice-bath and bromination was carried out in one hour using 0.26 mg (1.46 mmoles) of N-bromosuccinimide as the brominating agent to obtain a 44% yield of trimethylsilyl 3-bromomethyl-7-phenylacetamido-3-cephem-4-carboxylate-1-oxide.

EXAMPLE 89

0.1 mg (1 mmole) of amidosulfonic acid was added to the clear solution obtained by refluxing 75 ml of dichloromethane containing 0.76 g (3.3 mmoles) of N-trimethylsilylbenzenesulfonamide and 350 mg (1.0 mmole) of 3-methyl-7-phenylacetamido-3-cephem-4-carboxylic acid-1-oxide for one and a half hours and the mixture obtained was cooled in an ice-bath. Bromination was carried out in one hour with 0.26 g (1.46 mmoles) of N-bromosuccinimide as the brominating agent to obtain a 40% yield of trimethylsilyl 3-bromomethyl-7-phenylacetamido-3-cephem-4-carboxylate-1-oxide.

The following Examples illustrate the process of the invention followed by replacement of the bromine atom by a different substituent.

EXAMPLE 90

A solution of trimethylsilyl 3-methyl-7-phenylacetamido-3-cephem-4-carboxylate-1-oxide was prepared by refluxing a mixture consisting of 3.60 mg (10.2 mmoles) of 3-methyl-7-phenylacetamido-3-cephem-4-carboxylic acid-1-oxide, 1.20 ml (5.7 mmoles) of hexamethyldisilazane and 25 ml of dichloromethane for 3½ hours. The clear solution obtained was diluted to approximately 275 ml with dichloromethane and 0.2 g of amidosulfonic acid was added to it. After stirring for half an hour, the solution was cooled in an ice-bath and bromination was carried out in the usual way in one hour using 2.55 g (14.3 mmoles) of N-bromosuccinimide as the brominating agent.

A sample was withdrawn from the reaction mixture and analyzed by means of HPLC analysis and it was found that 54% of trimethylsilyl 3-bromomethyl-7-phenylacetamido-3-cephem-4-carboxylate-1-oxide and 11% of trimethylsilyl 2-bromo-3-bromomethyl-7-phenylacetamido-3-cephem-4-carboxylate-1-oxide had been formed.

To the remainder of the reaction mixture was added 0.75 ml of trimethyl phosphite (6 mmoles) and stirring was continued for 20 minutes. According to HPLC analysis the yield of trimethylsilyl 3-bromomethyl-7-phenylacetamido-3-cephem-4-carboxylate-1-oxide after this debromination reaction was 63%. 1.69 g of potassium 5-methyl-1,3,4-thiadiazole-2-thiolate (9.94 mmoles) were added to the remainder of the reaction mixture and after stirring for one hour at room temperature, the greenish reaction mixture was poured into a solution of 5 g of sodium bicarbonate in 100 ml of water. The pH of the mixture was adjusted to 7.5 by the addition of sodium bicarbonate and the water layer was separated. The organic layer was extracted twice with 50 ml of water and HPLC analysis of the combined water layers showed the yield of 3-(5-methyl-1,3,4-thiadiazolyl-2) thiomethyl-7-phenylacetamido-3-cephem-4-carboxylic acid-1-oxide to be 58%.

The pH of the water layer was adjusted to 6.0 and after extraction with two 50 ml of portions of ethyl acetate, the water layer was treated with activated carbon, filtered and acidified with 4 N sulfuric acid to a pH of 2.0. After storage overnight in the refrigerator, the precipitate was collected by filtration, washed with water and vacuum dried over phosphorus pentoxide to obtain 3.0 g of 3-(5-methyl-1,3,4-thiadiazoly-2)thiomethyl-7-phenylacetamido-3-cephem-4-carboxylic acid-1-oxide of 85.5% purity as determined by quantitative NMR Analysis, so the yield of isolated product was 54%. By HPLC analysis, it was shown that 4% of the product remained in the mother liquor.

220 Hz NMR Spectrum (DMSO-D6): 2.69 (s,3H); 3.52, 3.58, 3.67, 3.73 (ABq, 2H, J 13 Hz); 3.70, 3.78, 3.90, 3.98 (ABq, 2H, J 18 Hz); 4.09, 4.15, 4.70, 4.76 (ABq, 2H, J 13 Hz); 4.85 (d, 1H, J 4.5 Hz); 5.80 (dd, 1H, J 4.5 and 8.5 Hz); 7.32 (s, 5H); 8.34 (d, 1H, J 8.5 Hz).

IR Spectrum: 3280, 1775, 1723, 1658, 1520, 1498, 1453, 999 cm$^{-1}$.

The yield of trimethylsilyl 2-bromo-3-bromomethyl-7-phenylacetamido-3-cephem-4-carboxylate-1-oxide was determined in the same way as described for the 3'-bromo-cephalosporanic acid sulfoxide derivatives. The preparation of the methyl ester used as a reference compound is described in European patent application Ser. No. 78200174.7 published under No. 0001149.

EXAMPLE 91

To a suspension of 358 mg (1.03 mmoles) of 3-methyl-7-phenylacetamido-3-cephem-4-carboxylic acid-1-oxide in 25 ml of dichloromethane which was kept at room temperature, 322 mg (0.85 mmole) of bis-(trimethylsilyl)-bis-(trimethylsilyl)ethanediimidate were added in half an hour. A clear solution was obtained after stirring for 15 minutes more and stirring was continued for ¾ hour after which the solution was cooled in an ice-bath. Bromination was effected in half an hour using 290 mg (1.63 mmoles) of N-bromosuccinimide as the brominating agent.

A sample was withdrawn from the reaction mixture and analyzed in the usual way of HPLC analysis and a yield of 49% of trimethylsilyl 3-bromomethyl-7-phenylacetamido-3-cephem-4-carboxylate-1-oxide was found. To the remainder of the reaction mixture, 0.5 g of potassium 5-methyl-1,3,4-thiadiazole-2-thiolate (2.9 mmoles) was added and the mixture was stirred for 2 hours. 30 ml of water were added thereto and the pH of the mixture was adjusted to 7.0. The dichloromethane was evaporated in vacuo and the residue was diluted with acetone to 250 ml. According to HPLC analysis of this solution, the yield of 3-(5-methyl-1,3,4-thiadiazolyl-2)-thiomethyl-7-phenylacetamido-3-cephem-4-carboxylic acid-1-oxide was 50%.

Various modifications of the process of the invention may be made without departing from the spirit or scope thereof and it is to be understood that the invention is to be limited only as defined in the appended claims.

What we claim is:

1. A process for the preparation of 3'-bromo-substituted desacetoxycephalosporanic acid sulfoxide compounds comprising protecting the 4-carboxy group of a 3'-unsubstituted cephalosporanic acid sulfoxide by silylating in an inert anhydrous organic solvent with a silylating agent containing at least one nitrogen-bound silyl group and after neutralizing any base generated or left behind by the silyl donor, brominating the silylated compound in situ.

2. The process of claim 1 wherein the silylation is effected with a silylating agent having a silyl group of the formula

wherein R', R" and R'" are individually selected from the group consisting of alkyl of 1 to 6 carbon atoms optionally with halogen or an aryl.

3. The process of claim 2 wherein the silyl group is trimethylsilyl.

4. The process of claim 2 or 3 wherein the silylating agent is selected from the group consisting of a silazane and a silyl compound derived from an amide, urea, an amidosulfonate, a carbamate, a phosphorimidate, an imide, a hydantoin, a sulfonamide or a 2-oxazolidinone and a mixture of two or more of the said agents.

5. The process of claim 4 wherein the silylating agent is selected from the group consisting of hexamethyldisilazane, N,N'bis-(trimethylsilyl)-urea, N,O-bis-(trimethylsilyl)-acetamide, diethyl trimethylsilyl trimethylsilylphosphorimidate, trimethylsilyl trimethylsilylamidosulfonate, N-methyl-N-trimethylsilyltrifluoroacetamide, N,O-bis-(trimethylsilyl)-trifluoroacetamide, N-methyl-N-trimethylsilylacetamide, bis-(trimethylsilyl)-sulfate, N,N-bis-(trimethylsilyl)-formamide, trimethylsilyl trimethylsilylcarbamate, N-trimethylsilylacetamide, N-trimethylsilylcaprolactam, bis-(trimethylsilyl) bis-(trimethylsilyl)-ethanediimidate, N-trimethylsilylurethane, N-trimethylsilylphthalimide, N-trimethylsilylsuccinimide, N-trimethylsilyldiacetamide, N-trimethylsilylhexadydrophthalimide, 1,3-bis-(trimethylsilyl)-5,5-dimethylhydantoin, trimethylsilyl bis-(trimethylsilyl)amidosulfonate, N-trimethylsilyltrichloroacetamide, N-trimethylsilylbenzamide, N-trimethylsilyl-2-oxazolidinone, 1,3-bis-(trimethylsilyl)-hydantoin, N-trimethylsilyl-4-nitrobenzamide, N-trimethylsilyl-2,2-dimethylpropanamide and N-trimethylsilylbenzenesulfonamide and a mixture of two or more of the said agents.

6. The process of claim 1 wherein the bromination is effected with a member selected from the group consisting of an N-bromoamide, an N-bromoimide, an N-bromohydantoin and an N-bromo-2-oxazolidinone.

7. The process of claim 6 wherein the bromination is effected with a member selected from the group consisting of N-bromosuccinimide, N-bromophthalimide, 1,3-dibromo-5,5-dimethylhydantoin, 3-bromo-4,4-dimethyl-2-oxazolidinone, N-bromocaprolactam, N-bromoacetamide and N-bromo-3,3-dimethylglutarimide.

8. The process of claim 7 wherein the bromination is effected with N-bromosuccinimide or 1,3-dibromo-5,5-dimethylhydantoin.

9. The process of claim 1 wherein after the silylation has been effected, an acid is added in an amount at least sufficient to neutralize any base or bases present in the reaction mixture.

10. The process of claim 9 wherein the acid used is a member selected from the group consisting of carboxylic acid, a sulfonic acid and an inorganic acid.

11. The process of claim 10 wherein the acid used is a member selected from the group consisting of a lower carboxylic acid, a nitro- or halogen-substituted carboxylic acid, a sulfonic acid and a hydrogen halide.

12. The process of claim 10 or 11 wherein the acid used is a member selected from the group consisting of amidosulfonic acid, methanesulfonic acid, 10-camphorsulfonic acid, 4-chlorobenzenesulfonic acid, trichloroacetic acid, trifluoroacetic acid, formic acid, bromacetic acid, 2-chlorobenzoic acid, 4-nitrobenzoic acid, 4-nitrophenylacetic acid, α-chlorophenylacetic acid, p-toluene-sulfonic acid, sulfuric acid, hydrogen chloride and hydrogen bromide.

13. The process of claim 12 wherein the acid used is amidosulfonic acid.

14. The process of claim 1 wherein a compound is prepared of the formula

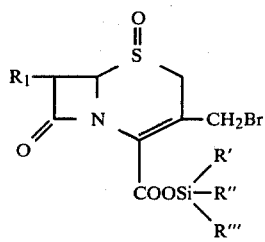
wherein R₁ represents an acylamido group and R′, R″ and R‴ are individually selected from the group consisting of alkyl of 1 to 6 carbon atoms optionally with a halogen or an aryl.
15. The process of claim 14 wherein R₁ is selected from the group consisting of benzamido, phenylacetamido, formamido and phenoxyacetamido.
16. The process of claim 14 or 15 wherein
is trimethylsilyl.
* * * * *